March 26, 1963 P. ECKE Plant Pat. 2,243
POINSETTIA PLANT
Filed May 28, 1962
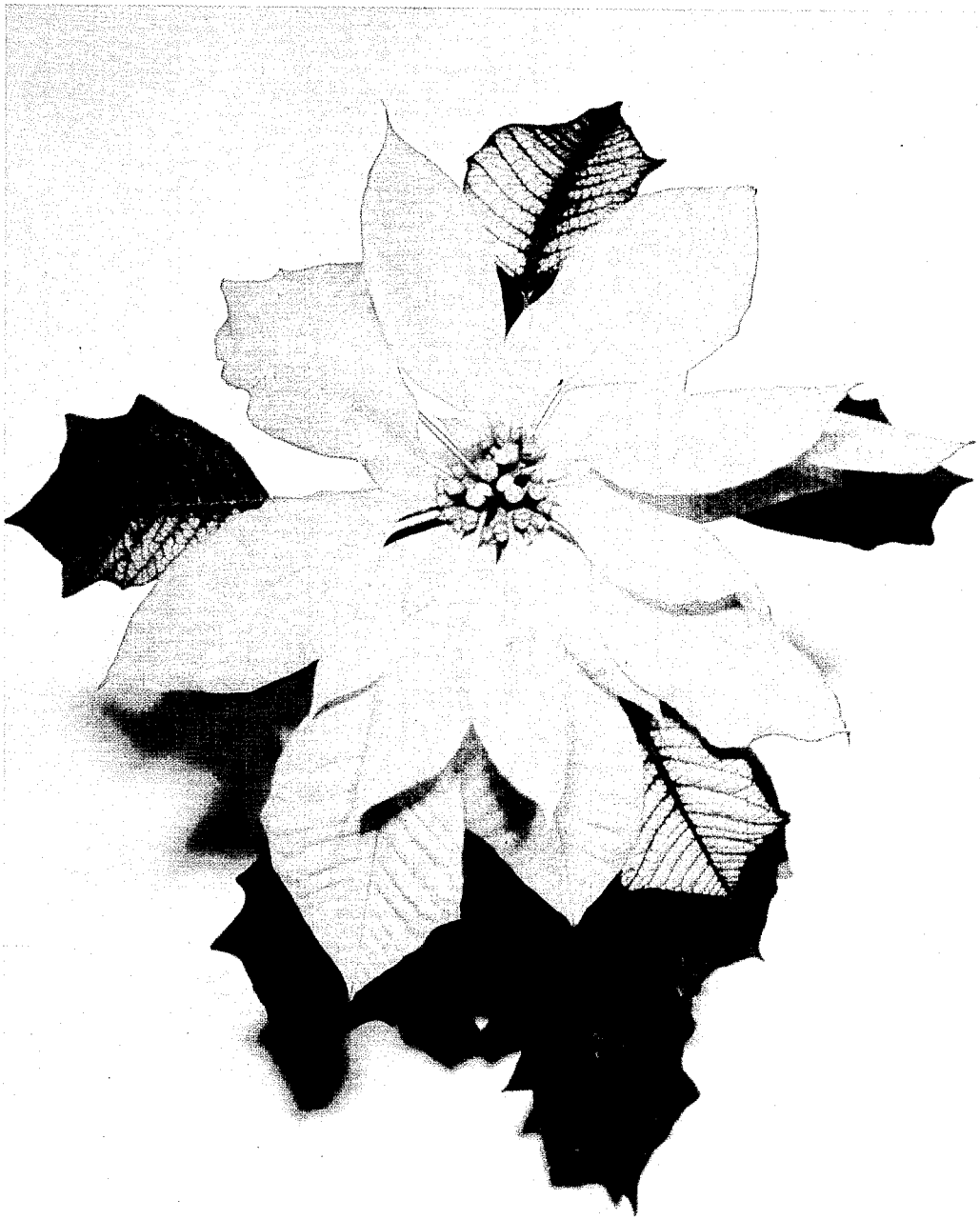
INVENTOR
PAUL ECKE
BY Wm. S. Trahan
ATTORNEY United States Patent Office Plant Pat. 2,243
Patented Mar. 26, 1963

2,243
POINSETTIA PLANT
Paul Ecke, P.O. Box 488, Encinitas, Calif.
Filed May 28, 1962, Ser. No. 198,383
1 Claim. (Cl. 47—60)

The present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly by its orange-tinted red color and the closely centered structure of the bract formation and inflorescence, and also to a substantial degree by its characteristic of propagation, in that it may be propagated through an exceptionally long season lasting through the usual propagation months of July and August, and also through the month of September, and still produce perfectly formed and uniformly colored bracts. To a lesser extent this new variety is differentiated from other varieties by its characteristic of relatively short peduncles providing a plant which has a great advantage in shipment.

The accompanying illustration, forming a part of this application and specification, graphically shows the predominant novelty of color and bract formation of this new variety, in color at substantially full maturity or optimum, the illustration being a perspective view taken from an angle above the plant, and therefore, illustrating substantially a full-faced view of the closely centered formation and the distinctive coloration of the bracts, as well as the foliage leaves.

The colors referred to herein have been designated in the specification by their usually applied non-technical terminology, but more exactly such colors correspond approximately with those shown in "Dictionary of Color" by Maerz & Paul (first edition 1930), and identified by the plate of said color standard as recapitulated in tabular form herein.

The following description more fully sets forth the characteristics of this new variety:

*Parentage*

This new variety was originated and discovered and cultivated by me in a cultivated area of a glassed-in nursery building at my experimental and growing garden at Encinitas, California, by means of cuttings. It originated as a cultivated sport of poinsettia plant of the variety usually designated in the trade as "Barbara Ecke Supreme" which is a patented variety described in my United States Letters Patent No. 1,055 dated December 18, 1951.

*Propagation*

In propagating this new variety and in asexually reproducing it, I have found it satisfactory and efficient to cut pieces of stalk of soft wood, substantially six inches in length, and to set such cuttings in beds of sand in the glass house of my nursery in or about the months of June, July, and August, and through the month of September, special note being made of the propagation of the new variety. In three or four weeks after planting the cuttings are well rooted and may be transferred to individual pots. My experience has been that the optimum temperature for growing under glass is of the order of 62 to 65 degrees F., night temperature, the daytime temperature being warmer, such as 70 to 75 degrees F., and subject to the varying conditions of light, heat, thickness of glass, cultivation, character of soil, fertilizer, and pruning or pinching.

*Asexual Reproduction*

This new variety of poinsettia plant has been repeatedly asexually reproduced and cultivated by me in my said glass house by cuttings, and successive reproductions thereof have remained true to type throughout the propagation, cultivation and asexual reproduction of several generations of the new variety, and it has shown its qualities and characteristics to be permanently fixed.

*Habits of Growth*

In this new variety of poinsettia plant the growth to optimum is developed with an appreciable variance of time. It may be propagated by cuttings during the months of June through the full month of September, a period of four months approximately, and yet all of those cuttings will reach a mature growth of bract involucre within a span of a period of about three weeks ranging from about December 5th to 25th, and will reach the commercial floral optimum about December 20th, which is about ten days later than the usual time of maturity to commercial floral optimum of most other varieties. It is a distinguishing characteristic of this new variety that even those plants which are propagated by cuttings planted through the month of September will produce bract involucres of normal and usual size, color, texture and distinctive characteristics equal to plants propagated by cuttings planted in the earlier months of June, July and August. As stated, this new variety reaches its optimum of growth in both plant structure and development of bracts approximately December 20th, and therefore, as compared with other varieties, it is a late-blooming variety by approximately a margin of at least 10 days, and more particularly is at least ten days later in reaching its optimum than its parent "Barbara Ecke Supreme" of my Patent No. 1,055. This late maturity to optimum has the commercial advantage that the optimum is reached nearer to the Christmas season, and also that it permits the plant to be grown under routine procedures instead of artificial mechanical light treatment as is customarily employed to bring plants to their optimum for the Christmas market. The bracts maintain their optimum for three to four weeks. This new variety is hardy and healthy in growth.

*Structure*

This new variety has a well developed spread of root structure. The peduncles or main stalks are of a medium brownish-green color and of quite rugged strength, which makes this variety stand shipment better than average. The normal average height of this new variety of plant is somewhat shorter than average, being in the range of three to four feet for field-grown plants. The internode spaces on the peduncle are below average in length making the plant close-jointed, though the number of foliage leaves on a main stalk are approximately average in number, giving a fully foliated appearance. At the top or axial end of the peduncle, grows a relatively large closely clustered inflorescence which is surrounded by the characteristic radiating bract involucre, the latter having a large number of bracts closely clustered centrally about the inflorescence, but definitely below the inflorescence which stands out distinctly at the center of the bract involucre.

*Bracts*

One of the principal novel characteristics of this new variety of poinsettia plants which distinguishes it from its parent plant and other known varieties is the structural formation and coloration of the bract involucre. Though the bracts vary in size of planar area, they are exceptionally uniform in their shape throughout the planar area of the individual bracts, and they have a general uniformity of color shading in the plane of the individual bracts, more so than is usually present in poinsettia plants. In coloration, the bracts are a deep red uniform hue, closely approximating what is designated by Maerz & Paul as Raspberry Red as shown at Plate 3–K–9 of that color authority. By way of color comparison, the bracts are more nearly the color of the parent plant of my Patent No. 1,055, though of a somewhat lighter shade.

In shape of planar outline, the individual bracts are elongated and ovately-acuminate, more nearly resembling the shape of bracts in my Plant Patent No. 1,779 of December 9, 1958, though the color in this new variety is a much more subdued red and having a greater influence of orange or burnt-orange tint than the brilliant pink-red tint of said Patent No. 1,779.

The arrangement of the bracts in this new variety is characterized by an involucre in which the edges of adjacent individual bracts are in overlying relation radiating from the inflorescence. In the involucre there is a substantial number of the bracts which have quite long petioles which space those bracts from the inflorescence; and there are other bracts which have very short acaulescent petioles which space these bracts close to the center of the involucre and closely centered around the inflorescence. Thus the involucre of the bract, as a whole, is expanded in overall diameter by the bracts having the longer petioles, and is also closely centered around the inflorescence by the bracts having the shorter petioles.

In physical arrangement the involucre of the bracts of the present variety more nearly approximates the physical arrangement of bracts in my Plant Patent No. 1,068 of January 28, 1952, differing, however, in respects of color, the more general uniformity of shape of the individual bracts of the present new variety, the close centering of the bracts around the abundant inflorescence, and the wider spread of diameter of the involucre with less overlapping of the relatively next adjacent bracts which provides more of a single-layer appearance of the involucre.

As stated under the heading of growth habit, the bract involucre under normal conditions of growth reaches an optimum about December 20th, even with respect to plants propagated by planting through the month of September, and the bract involucre of those late propagated plants will be as perfect as those of the plants propagated in earlier months. The optimum is therefore about 10 days later than the usual poinsettia plant, a very decided advantage in shipment to commercial markets for the Christmas and holiday season. Having reached its optimum, the involucre is long-lasting and will retain that condition for substantially four weeks.

*Inflorescence*

An inflorescence grows upon the axial free terminal end of the peduncle and centrally of the bract involucre, as is usual. The inflorescence is relatively large and well defined, quite prominent, and forms a central rosette from which the closely centered bracts radiate. The inflorescence grows on small pale-green spurs, and the flower grows on short sub-acaulescent stems. As is usual in a large number of varieties of poinsettia plants, the cyathium is of pale green color, small and not prominent, and the flower growing therefrom is orange-yellow in color, with a touch of crimson red, common generally to the inflorescence of poinsettia plants.

*Foliage*

The foliage leaves are of the usual number and arranged around the peduncle. Because of the diminished height of the plant, the nodes of the foliage leaves are more closely spaced than in the poinsettia plants of greater height. As in many varieties of poinsettia plants, the foliage leaves are not entirely uniform in shape, but are generally oblate-ovate at the pedicel-end, and having a plurality of oak-leaf points at the outer end. The petioles of the foliage leaves are rather long, and the venation is of herringbone type. The color of the foliage leaves which are remote from the bract involucre may be broadly described as medium dark ivy green. A few of the foliage leaves next adjacent to the involucre may be and usually are either in their entirety or partially, splashed with color simulating the color of the bracts. However, this is not an uncommon phenomenon in known varieties of poinsettia plants.

*Variations*

Different individual plants of this new variety have an unusual similarity of adherence to characteristics and type herein described. However, there may be some variation in the characteristics of minor details, in comparison of plants grown in various localities, in different soils, and at different times of the year, varying temperatures, varying types of glass house, or out of doors.

*Color Tabulation*

The color designations according to the color plates of the aforesaid "Dictionary of Color" are recapitulated in tabular form as follows:

| Part of Plant | Non-Technical Designation of Color | Dictionary of Color | | |
|---|---|---|---|---|
| | | Plate | Letter | Number |
| Peduncle | Brownish green | 14 | L | 7 |
| Bracts | Deep red, faintly orange tinted. | 3 | K | 9 |
| Foliage leaves: | | | | |
| (a) remote from bracts. | Dark ivy green | 24 | A | 12 |
| (b) adjacent to bracts. | Partially or wholly substantially same as bracts. | 3 | K | 9 |
| Inflorescence: | | | | |
| (a) cyathium | Pale green | 17 | I | 7 |
| (b) flower | Orange yellow | 10 | L | 5 |
| (c) center portion | Crimson red | 41 | L | 1 |

Having thus described the new variety of poinsettia plant of my invention and discovery, I claim:

A new and distinct variety of poinsettia plant, substantially as illustrated and described, characterized by an involucre of bracts of deep red color which is generally uniform throughout the bracts of the involucre, the bracts being prolately ovate-acuminate, and having a portion of the bracts on relatively long petioles which space such bracts from the center of the involucre, and other bracts on relatively short petioles which cluster the pedicel ends thereof closely to the center of the involucre, a well-developed and profuse inflorescence at the center of the involucre substantially closing the opening at said center thereof, this new variety being further characterized by a closer spacing of nodes of foliage leaves which provides a plant of relatively less vertical height than the usual known variety of poinsettia plant, and further characterized by the faculty of producing the optimum of its bract involucre approximately 10 days later than other known varieties, and more particularly, by the production of a bract involucre which is equally perfect on plants of late propagation of cuttings in September as on plants of earlier propagation of cutting in the usual season of propagation in June, July and August.

No references cited.